(12) United States Patent
Johnson

(10) Patent No.: US 9,283,028 B2
(45) Date of Patent: Mar. 15, 2016

(54) CREST-FACTOR CONTROL OF PHASE-SHIFTED INVERTER

(71) Applicant: COVIDIEN LP, Mansfield, MA (US)

(72) Inventor: Joshua H. Johnson, Arvada, CO (US)

(73) Assignee: Covidien LP, Mansfield, MA (US)

( * ) Notice: Subject to any disclaimer, the term of this patent is extended or adjusted under 35 U.S.C. 154(b) by 307 days.

(21) Appl. No.: 14/098,859

(22) Filed: Dec. 6, 2013

(65) Prior Publication Data

US 2014/0276749 A1 Sep. 18, 2014

Related U.S. Application Data

(60) Provisional application No. 61/789,080, filed on Mar. 15, 2013.

(51) Int. Cl.
*A61B 18/12* (2006.01)
*A61B 18/18* (2006.01)
*A61B 18/00* (2006.01)

(52) U.S. Cl.
CPC .............. *A61B 18/1206* (2013.01); *A61B 18/18* (2013.01); *A61B 2018/00726* (2013.01); *A61B 2018/00892* (2013.01); *A61B 2018/1286* (2013.01)

(58) Field of Classification Search
CPC ........... A61B 18/1206; A61B 18/1233; A61B 2018/00726; A61B 2018/00767; A61B 2018/00892; A61B 2018/1256
See application file for complete search history.

(56) References Cited

U.S. PATENT DOCUMENTS

| 3,514,689 A | 5/1970 | Giannamore |
| 3,641,422 A | 2/1972 | Farnsworth et al. |
| 3,801,800 A | 4/1974 | Newton |
| 3,885,569 A | 5/1975 | Judson |
| 3,897,787 A | 8/1975 | Ikuno et al. |
| 3,978,393 A | 8/1976 | Wisner et al. |
| 4,102,341 A | 7/1978 | Ikuno et al. |

(Continued)

FOREIGN PATENT DOCUMENTS

| DE | 179607 C | 3/1905 |
| DE | 390937 C | 3/1924 |

(Continued)

OTHER PUBLICATIONS

European Search Report No. 14166165.2 dated Jul. 8, 2014.

(Continued)

*Primary Examiner* — Michael Peffley

(57) ABSTRACT

A method for controlling an electrosurgical generator includes generating at least one electrosurgical waveform at a selected energy setting through an RF output stage comprising an RF inverter coupled to a power source. The at least one electrosurgical waveform has a duty cycle and a crest factor. The method also includes adjusting a repetition rate of the at least one electrosurgical waveform based on the selected energy setting to regulate the duty cycle of the at least one electrosurgical waveform. The method also includes applying the at least one electrosurgical waveform to tissue through at least one electrode and measuring an output voltage of the at least one electrosurgical waveform. The method also includes supplying a control signal to the RF inverter based on the repetition rate when the output voltage is increasing to regulate the crest factor of the at least one electrosurgical waveform.

20 Claims, 5 Drawing Sheets

(56) References Cited

U.S. PATENT DOCUMENTS

| | | |
|---|---|---|
| 4,287,557 A | 9/1981 | Brehse |
| 4,378,801 A | 4/1983 | Oosten |
| 4,416,276 A | 11/1983 | Newton et al. |
| 4,416,277 A | 11/1983 | Newton et al. |
| 4,430,625 A | 2/1984 | Yokoyama |
| 4,436,091 A | 3/1984 | Banko |
| 4,438,766 A | 3/1984 | Bowers |
| 4,559,943 A | 12/1985 | Bowers |
| 4,569,345 A | 2/1986 | Manes |
| 4,572,190 A | 2/1986 | Azam et al. |
| 4,590,934 A | 5/1986 | Malis et al. |
| 4,630,218 A | 12/1986 | Hurley |
| 4,644,955 A | 2/1987 | Mioduski |
| 4,658,815 A | 4/1987 | Farin et al. |
| 4,658,820 A | 4/1987 | Klicek |
| 4,691,703 A | 9/1987 | Auth et al. |
| 4,739,759 A | 4/1988 | Rexroth et al. |
| 4,754,757 A | 7/1988 | Feucht |
| 4,767,999 A | 8/1988 | VerPlanck |
| 4,860,745 A | 8/1989 | Farin et al. |
| 5,075,839 A | 12/1991 | Fisher et al. |
| 5,119,284 A | 6/1992 | Fisher et al. |
| 5,304,917 A | 4/1994 | Somerville |
| 5,318,563 A | 6/1994 | Malis et al. |
| 5,334,183 A | 8/1994 | Wuchinich |
| 5,370,672 A | 12/1994 | Fowler et al. |
| 5,372,596 A | 12/1994 | Klicek et al. |
| 5,396,194 A | 3/1995 | Williamson et al. |
| 5,438,302 A | 8/1995 | Goble |
| 5,472,443 A * | 12/1995 | Cordis ............... A61B 18/1206 606/32 |
| 5,500,616 A | 3/1996 | Ochi |
| 5,531,774 A | 7/1996 | Schulman et al. |
| 5,540,684 A | 7/1996 | Hassler, Jr. |
| 5,558,671 A | 9/1996 | Yates |
| 5,559,688 A | 9/1996 | Pringle |
| 5,596,466 A | 1/1997 | Ochi |
| 5,658,322 A | 8/1997 | Fleming |
| 5,674,217 A | 10/1997 | Wahlstrom et al. |
| 5,694,304 A | 12/1997 | Telefus et al. |
| 5,712,772 A | 1/1998 | Telefus et al. |
| 5,729,448 A | 3/1998 | Haynie et al. |
| 5,777,519 A | 7/1998 | Simopoulos |
| 5,792,138 A | 8/1998 | Shipp |
| 5,817,093 A | 10/1998 | Williamson, IV et al. |
| 5,871,481 A | 2/1999 | Kannenberg et al. |
| 5,936,446 A | 8/1999 | Lee |
| 6,017,354 A | 1/2000 | Culp et al. |
| 6,044,283 A | 3/2000 | Fein et al. |
| 6,063,075 A | 5/2000 | Mihori |
| 6,090,123 A | 7/2000 | Culp et al. |
| 6,142,992 A | 11/2000 | Cheng et al. |
| 6,162,217 A | 12/2000 | Kannenberg et al. |
| 6,222,356 B1 | 4/2001 | Taghizadeh-Kaschani |
| 6,235,020 B1 | 5/2001 | Cheng et al. |
| 6,243,654 B1 | 6/2001 | Johnson et al. |
| 6,296,636 B1 | 10/2001 | Cheng et al. |
| 6,329,778 B1 | 12/2001 | Culp et al. |
| 6,426,886 B1 | 7/2002 | Goder |
| 6,693,782 B1 | 2/2004 | Lash |
| 6,723,091 B2 | 4/2004 | Goble et al. |
| 6,740,079 B1 | 5/2004 | Eggers et al. |
| 6,819,027 B2 | 11/2004 | Saraf |
| 6,923,804 B2 | 8/2005 | Eggers et al. |
| 6,936,047 B2 | 8/2005 | Nasab et al. |
| 7,004,174 B2 | 2/2006 | Eggers et al. |
| 7,041,096 B2 | 5/2006 | Malis et al. |
| 7,324,357 B2 | 1/2008 | Miura et al. |
| 7,364,972 B2 | 4/2008 | Ono et al. |
| D574,323 S | 8/2008 | Waaler |
| 7,422,582 B2 | 9/2008 | Malackowski et al. |
| 7,511,472 B1 | 3/2009 | Xia et al. |
| 7,517,351 B2 | 4/2009 | Culp et al. |
| 7,651,492 B2 * | 1/2010 | Wham ............... A61B 18/1206 606/34 |
| 7,794,457 B2 | 9/2010 | McPherson et al. |
| 7,863,841 B2 | 1/2011 | Menegoli et al. |
| 8,045,943 B2 | 10/2011 | Kaczman et al. |
| 8,162,932 B2 * | 4/2012 | Podhajsky ......... A61B 18/1206 606/34 |
| 2009/0248007 A1 | 10/2009 | Falkenstein et al. |
| 2010/0268220 A1 | 10/2010 | Johnson et al. |
| 2011/0071518 A1 | 3/2011 | Gilbert |
| 2011/0087213 A1 | 4/2011 | Messerly et al. |
| 2011/0115562 A1 | 5/2011 | Gilbert |
| 2013/0035679 A1 | 2/2013 | Orszulak |
| 2013/0053840 A1 | 2/2013 | Krapohl et al. |
| 2013/0066311 A1 | 3/2013 | Smith et al. |
| 2013/0067725 A1 | 3/2013 | Behnke, II et al. |
| 2013/0072920 A1 | 3/2013 | Behnke, II et al. |
| 2013/0072921 A1 | 3/2013 | Behnke, II et al. |
| 2013/0072922 A1 | 3/2013 | Behnke, II et al. |
| 2013/0072923 A1 | 3/2013 | Behnke, II et al. |
| 2013/0079673 A1 | 3/2013 | Stein et al. |
| 2013/0190751 A1 | 7/2013 | Brannan |
| 2013/0193952 A1 | 8/2013 | Krapohl |
| 2013/0197510 A1 | 8/2013 | Heckel |
| 2013/0197874 A1 | 8/2013 | Heckel |
| 2013/0249721 A1 | 9/2013 | Smith |
| 2013/0253501 A1 | 9/2013 | Joseph |
| 2013/0261616 A1 | 10/2013 | Prakash et al. |
| 2013/0267944 A1 | 10/2013 | Krapohl |
| 2013/0274729 A1 | 10/2013 | Orszulak |
| 2013/0304049 A1 | 11/2013 | Behnke, II et al. |
| 2013/0345696 A1 | 12/2013 | Behnke, II et al. |
| 2014/0002056 A1 | 1/2014 | Moul et al. |
| 2014/0015535 A1 | 1/2014 | Lopez |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2602517 A1 | 7/1976 |
| DE | 2504280 A1 | 8/1976 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 3904558 A1 | 8/1990 |
| DE | 3942998 A1 | 7/1991 |
| DE | 4206433 A1 | 9/1993 |
| DE | 4339049 A1 | 5/1995 |
| DE | 19506363 A1 | 8/1996 |
| DE | 19717411 A1 | 11/1998 |
| DE | 19848540 A1 | 5/2000 |
| DE | 10 2008058737 A1 | 4/2010 |
| EP | 0 246 350 A1 | 11/1987 |
| EP | 267403 A2 | 5/1988 |
| EP | 296777 A2 | 12/1988 |
| EP | 310431 A2 | 4/1989 |
| EP | 325456 A2 | 7/1989 |
| EP | 336742 A2 | 10/1989 |
| EP | 390937 A1 | 10/1990 |
| EP | 0 556 705 A1 | 8/1993 |
| EP | 608609 A2 | 8/1994 |
| EP | 694291 A1 | 1/1996 |
| EP | 0 836 868 A2 | 4/1998 |
| EP | 880220 A1 | 11/1998 |
| EP | 0 882 955 A1 | 12/1998 |
| EP | 1051948 A2 | 11/2000 |
| EP | 1151725 A1 | 11/2001 |
| EP | 1157667 A2 | 11/2001 |
| EP | 1366724 A1 | 12/2003 |

(56) References Cited

FOREIGN PATENT DOCUMENTS

| EP | 1500378 A1 | 1/2005 |
|---|---|---|
| EP | 1681026 A2 | 7/2006 |
| EP | 1776929 A1 | 4/2007 |
| EP | 2100566 A1 | 9/2009 |
| EP | 2393208 A2 | 12/2011 |
| EP | 2469699 A2 | 6/2012 |
| FR | 1 275 415 A | 11/1961 |
| FR | 1 347 865 A | 1/1964 |
| FR | 2 313 708 A1 | 12/1976 |
| FR | 2364461 A1 | 4/1978 |
| FR | 2 502 935 A1 | 10/1982 |
| FR | 2 517 953 A1 | 6/1983 |
| FR | 2 573 301 A1 | 5/1986 |
| GB | 1290304 A | 9/1972 |
| GB | 2434872 A | 8/2007 |
| JP | 63 005876 A | 1/1988 |
| JP | 2002-065690 A | 3/2002 |
| JP | 2005-185657 A | 7/2005 |
| SU | 166452 | 11/1964 |
| SU | 727201 A2 | 4/1980 |
| WO | 02/11634 A1 | 2/2002 |
| WO | 02/45589 A2 | 6/2002 |
| WO | 03/090635 A1 | 11/2003 |
| WO | 2006/050888 A1 | 5/2006 |
| WO | 2008/043999 A2 | 4/2008 |
| WO | 2008/053532 A1 | 5/2008 |
| WO | 2008135736 A1 | 11/2008 |

OTHER PUBLICATIONS

Wald et al., "Accidental Burns", JAMA, Aug. 16, 1971, vol. 217, No. 7, pp. 916-921.
Vallfors et al., "Automatically Controlled Bipolar Electrosoagulation—'COA-COMP'", Neurosurgical Review 7:2-3 (1984) pp. 187-190.
Sugita et al., "Bipolar Coagulator with Automatic Thermocontrol", J. Neurosurg., vol. 41, Dec. 1944, pp. 777-779.
Prutchi et al. "Design and Development of Medical Electronic Instrumentation", John Wiley & Sons, Inc. 2005.
Momozaki et al. "Electrical Breakdown Experiments with Application to Alkali Metal Thermal-to-Electric Converters", Energy conversion and Management; Elsevier Science Publishers, Oxford, GB; vol. 44, No. 6, Apr. 1, 2003 pp. 819-843.
Muller et al. "Extended Left Hemicolectomy Using the LigaSure Vessel Sealing System", Innovations That Work; Company Newsletter; Sep. 1999.
Ogden Goertzel Alternative to the Fourier Transform: Jun. 1993 pp. 485-487, Electronics World; Reed Business Publishing, Sutton, Surrey, BG vol. 99, No. 9. 1687.
Hadley I C D et al., "Inexpensive Digital Thermometer for Measurements on Semiconductors", International Journal of Electronics; Taylor and Francis. Ltd.; London, GB; vol. 70, No. 6 Jun. 1, 1991; pp. 1155-1162.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Richard Wolf Medical Instruments Corp. Brochure, "Kleppinger Bipolar Forceps & Bipolar Generator", 3 pp. Jan. 1989.
Astrahan, "A Localized Current Field Hyperthermia System for Use with 192-Iridium Interstitial Implants" Medical Physics, 9 (3), May/Jun. 1982.

Alexander et al., "Magnetic Resonance Image-Directed Stereotactic Neurosurgery: Use of Image Fusion with Computerized Tomography to Enhance Spatial Accuracy", Journal Neurosurgery, 83; (1995) pp. 271-276.
Geddes et al., "The Measurement of Physiologic Events by Electrical Impedence", Am. J. MI, Jan. Mar. 1964, pp. 16-27.
Cosman et al., "Methods of Making Nervous System Lesions", In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Cosman et al., "Radiofrequency Lesion Generation and its Effect on Tissue Impedance", Applied Neurophysiology 51: (1988) pp. 230-242.
Zlatanovic M., "Sensors in Diffusion Plasma Processing" Microelectronics 1995; Proceedings 1995; 20th International Conference CE on Nis, Serbia Sep. 12-14, 1995; New York, NY vol. 2 pp. 565-570.
Ni W. et al. "A Signal Processing Method for the Coriolis Mass Flowmeter Based on a Normalized...", Journal of Applied Sciences-Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297, Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone", Neurosurgery 15: (1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300", 1 p. Sep. 1998.
Valleylab Brochure "Valleylab Electroshield Monitoring System", 2 pp. Nov. 1995.
Extended European Search Report from Application No. EP 14156761.0 dated Jul. 7, 2014.
European Search Report No. 14158040 dated May 26, 2014.
U.S. Appl. No. 10/406,690, filed Apr. 3, 2003, Michael S. Klicek.
U.S. Appl. No. 10/573,713, filed Mar. 28, 2006, Robert H. Wham.
U.S. Appl. No. 10/761,524, filed Jan. 21, 2004, Robert Wham.
U.S. Appl. No. 11/242,458, filed Oct. 3, 2005, Daniel J. Becker.
U.S. Appl. No. 13/943,518, filed Jul. 16, 2013, Orszulak et al.
U.S. Appl. No. 13/971,553, filed Aug. 20, 2013, Behnke.
U.S. Appl. No. 13/971,596, filed Aug. 20, 2013, Collins.
U.S. Appl. No. 14/048,946, filed Oct. 3, 2013, Wham.
U.S. Appl. No. 14/058,929, filed Oct. 21, 2013, Gilbert.
U.S. Appl. No. 14/058,957, filed Oct. 21, 2013, Gilbert.
U.S. Appl. No. 14/069,534, filed Nov. 1, 2013, Digmann.
U.S. Appl. No. 14/072,312, filed Nov. 5, 2013, Wham.
U.S. Appl. No. 14/072,342, filed Nov. 5, 2013, Wham.
U.S. Appl. No. 14/072,386, filed Nov. 5, 2013, Wham.
U.S. Appl. No. 14/096,341, filed Dec. 4, 2013, Johnson.
U.S. Appl. No. 14/098,859, filed Dec. 6, 2013, Johnson.
U.S. Appl. No. 14/100,113, filed Dec. 9, 2013, Gilbert.
U.S. Appl. No. 14/144,850, filed Dec. 31, 2013, Johnston.
U.S. Appl. No. 14/147,294, filed Jan. 3, 2014, Gilbert.
U.S. Appl. No. 14/147,312, filed Jan. 3, 2014, Gilbert.

* cited by examiner

CREST-FACTOR CONTROL OF PHASE-SHIFTED INVERTER

CROSS REFERENCE TO RELATED APPLICATION

The present application claims the benefit of and priority to U.S. Provisional Application Ser. No. 61/789,080, filed on Mar. 15, 2013, the entire contents of which are incorporated herein by reference.

BACKGROUND

1. Technical Field

The present disclosure relates to an electrosurgical system and method for operating an electrosurgical generator. More particularly, the present disclosure relates to a system, method and apparatus for controlling electrosurgical waveforms generated by a radiofrequency resonant inverter that are suitable for arc cutting and coagulation.

2. Background of Related Art

Electrosurgery involves application of high radio frequency electrical current to a surgical site to cut, ablate, or coagulate tissue. In monopolar electrosurgery, a source or active electrode delivers radio frequency alternating current from the electrosurgical generator to the targeted tissue and a return electrode conducts the current back to the generator. A patient return electrode is placed remotely from the active electrode to conduct the current back to the generator.

In bipolar electrosurgery return and active electrodes are placed in close proximity to each other such that an electrical circuit is formed between the two electrodes (e.g., in the case of an electrosurgical forceps). In this manner, the applied electrical current is limited to the body tissue positioned between the electrodes. Accordingly, bipolar electrosurgery generally involves the use of instruments where it is desired to achieve a focused delivery of electrosurgical energy between two electrodes positioned on the instrument, e.g. forceps or the like. A forceps is a pliers-like instrument which relies on mechanical action between its jaws to grasp, clamp and constrict vessels or tissue. Electrosurgical forceps (open or endoscopic) utilize mechanical clamping action and electrical energy to effect hemostasis on the clamped tissue. The forceps include electrosurgical conductive surfaces which apply the electrosurgical energy to the clamped tissue. By controlling the intensity, frequency and duration of the electrosurgical energy applied through the conductive plates to the tissue, the surgeon can coagulate and/or seal tissue. However, the above example is for illustrative purposes only and there are many other known bipolar electrosurgical instruments which are within the scope of the present disclosure.

Electrosurgical procedures outlined above may utilize various tissue and energy parameters in a feedback-based control system. There is continual need to improve delivery of energy to the tissue.

SUMMARY

According to one embodiment, the present disclosure provides for a method for controlling an electrosurgical generator. The method includes generating at least one electrosurgical waveform at a selected energy setting through an RF output stage comprising an RF inverter coupled to a power source. The at least one electrosurgical waveform has a duty cycle and a crest factor. The method also includes adjusting a repetition rate of the at least one electrosurgical waveform based on the selected energy setting to regulate the duty cycle of the at least one electrosurgical waveform; applying the at least one electrosurgical waveform to tissue through at least one electrode; measuring an output voltage of the at least one electrosurgical waveform; and supplying a control signal to the RF inverter based on the repetition rate when the output voltage is increasing to regulate the crest factor of the at least one electrosurgical waveform.

According to one aspect of the above-embodiment, the method further includes calculating a peak value of the output voltage and supplying the control signal to the RF inverter prior to the output voltage reaching the peak value.

According to one aspect of the above-embodiment, the peak value of the output voltage is changed based on the supplying of the control signal to the RF inverter.

According to one aspect of the above-embodiment, the energy setting is at least one of power, current, and voltage.

According to one aspect of the above-embodiment, the RF inverter comprises at least one switching element coupled to a controller.

According to one aspect of the above-embodiment, the control signal is a phase-shifted drive signal generated by a pulse-width modulated driver for controlling the at least one switching element.

According to one aspect of the above-embodiment, the method further includes increasing the repetition rate of the at least one electrosurgical waveform to decrease the duty cycle of the at least one electrosurgical waveform.

According to another embodiment, the present disclosure provides for an electrosurgical generator. The generator includes an RF output stage comprising an RF inverter coupled to a power source, the RF output stage configured to generate at least one electro surgical waveform at a selected energy setting, the at least one electrosurgical waveform having a duty cycle and a crest factor; a controller configured to adjust a repetition rate of the at least one electrosurgical waveform based on the selected energy setting to regulate the duty cycle of the at least one electrosurgical waveform; and a sensor configured to measure an output voltage of the at least one electrosurgical waveform, the controller configured to supply a control signal to the RF inverter based on the repetition rate when the output voltage is increasing to regulate the crest factor of the at least one electrosurgical waveform.

According to one aspect of the above-embodiment, the controller is further configured to calculate a peak value of the output voltage and supply the control signal to the RF inverter prior to the output voltage reaching the peak value.

According to one aspect of the above-embodiment, the peak value of the output voltage is changed based on the supplying of the control signal to the RF inverter.

According to one aspect of the above-embodiment, the energy setting is at least one of power, current, and voltage.

According to one aspect of the above-embodiment, the RF inverter comprises at least one switching element coupled to the controller.

According to one aspect of the above-embodiment, the control signal is a phase-shifted drive signal generated by a pulse-width modulated driver for controlling the at least one switching element.

According to one aspect of the above-embodiment, the controller is configured to increase the repetition rate of the at least one electrosurgical waveform to decrease the duty cycle of the at least one electrosurgical waveform.

According to another embodiment, the present disclosure provides for an electrosurgical system. The system includes an electrosurgical generator. The generator includes an RF output stage comprising an RF inverter coupled to a power source, the RF output stage configured to generate at least one electrosurgical waveform at a selected energy setting, the at least one electro surgical waveform having a duty cycle and a crest factor; a controller configured to adjust a repetition rate of the at least one electrosurgical waveform based on the selected energy setting to regulate the duty cycle of the at least one electrosurgical waveform; and a sensor configured to measure an output voltage of the at least one electrosurgical waveform, the controller configured to supply a control signal to the RF inverter based on the repetition rate when the output voltage is increasing to regulate the crest factor of the at least one electrosurgical waveform.

According to one aspect of the above-embodiment, the controller is further configured to calculate a peak value of the output voltage and supply the control signal to the RF inverter prior to the output voltage reaching the peak value.

According to one aspect of the above-embodiment, the peak value of the output voltage is changed based on the supplying of the control signal to the RF inverter.

According to one aspect of the above-embodiment, the energy setting is at least one of power, current, and voltage.

According to one aspect of the above-embodiment, the RF inverter comprises at least one switching element coupled to the controller.

According to one aspect of the above-embodiment, the control signal is a phase-shifted drive signal generated by a pulse-width modulated driver for controlling the at least one switching element.

According to another embodiment, the present disclosure provides for a method for controlling an electrosurgical generator. The method includes generating at least one electrosurgical waveform at a selected energy setting through an RF output stage coupled to a power source, the RF output stage comprising an RF inverter having a resonant network. The at least one electrosurgical waveform has a duty cycle and a crest factor. The method also includes adjusting a repetition rate of the at least one electrosurgical waveform based on the selected energy setting to regulate the duty cycle of the at least one electrosurgical waveform; applying the at least one electrosurgical waveform to tissue through at least one electrode; measuring an output voltage of the at least one electrosurgical waveform; and supplying a control signal to the RF inverter based on the repetition rate to match a peak, e.g., a positive peak, of the output voltage to an inverse peak, e.g., a negative peak, of a tank voltage across the resonant network.

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

A generator according to the present disclosure can perform monopolar and/or bipolar electrosurgical procedures, including, for example, cutting, coagulation, ablation, and vessel sealing procedures. The generator may include a plurality of outputs for interfacing with various electrosurgical instruments (e.g., a monopolar instrument, return electrode, bipolar electrosurgical forceps, footswitch, etc.). Further, the generator includes electronic circuitry configured to generate radio frequency energy specifically suited for various electrosurgical modes (e.g., cut, blend, coagulate, division with hemostasis, fulgurate, spray, etc.) and procedures (e.g., monopolar, bipolar, vessel sealing). In embodiments, the generator may be embedded, integrated or otherwise coupled to the electrosurgical instruments providing for an all-in-one electrosurgical apparatus.

Figure 1:
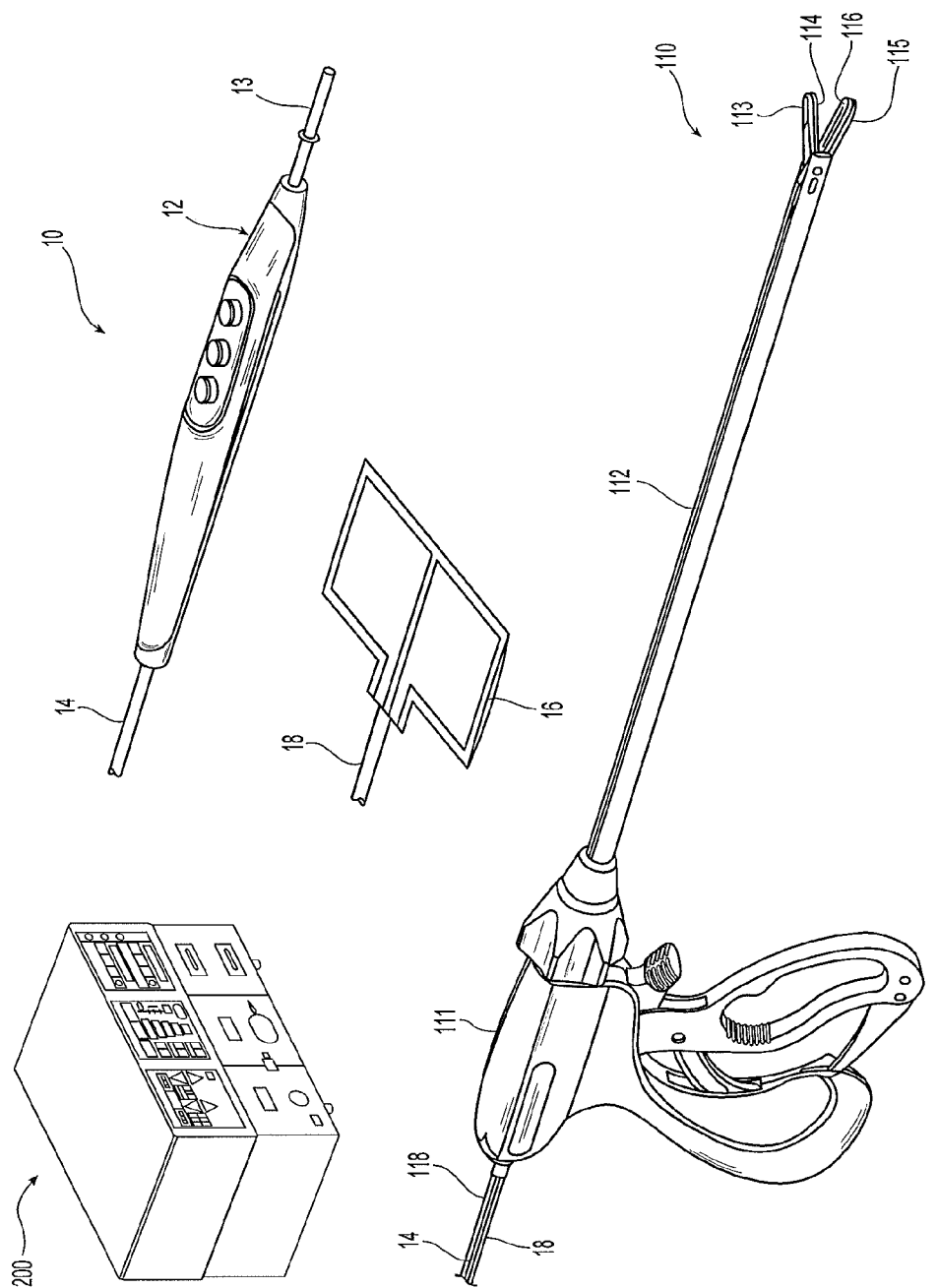
FIG. 1 is a perspective view of the components of one illustrative embodiment of an electrosurgical system according to the present disclosure.

FIG. 1 is an illustration of a bipolar and monopolar electrosurgical system 10 according to the present disclosure. The system 10 may include one or more monopolar electrosurgical instruments 12 having one or more active electrodes 13 (e.g., electrosurgical cutting probe, ablation electrode(s), etc.) for treating tissue of a patient. Electrosurgical alternating current is supplied to the instrument 12 by a generator 200 via a supply line 14 that is connected to an active terminal 230 (FIG. 3) of the generator 200, allowing the instrument 12 to cut, coagulate, ablate and/or otherwise treat tissue. The alternating current is returned to the generator 200 through a return electrode pad 16 via a return line 18 at a return terminal 232 (FIG. 3) of the generator 200. For monopolar operation, the system 10 may include a plurality of return electrode pads 16 that, in use, are disposed on a patient to minimize the chances of tissue damage by maximizing the overall contact area with the patient. In addition, the generator 200 and the return electrode pads 16 may be configured for monitoring so-called "tissue-to-patient" contact to insure that sufficient contact exists therebetween to further minimize chances of tissue damage.

Figure 3:
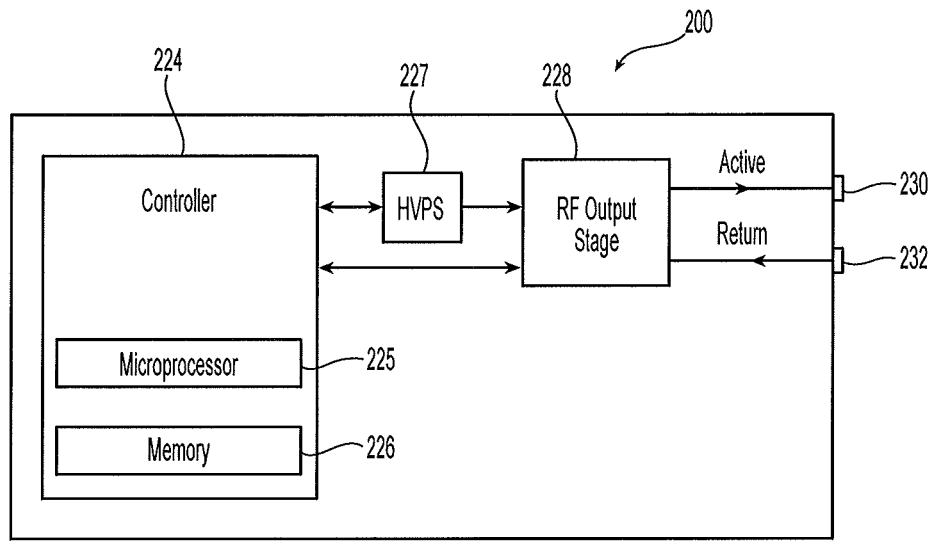
FIG. 3 is a schematic, block diagram of the embodiment of an electrosurgical generator of FIG. 2 according to the present disclosure.

The system 10 may also include one or more bipolar electrosurgical instruments, for example, a bipolar electrosurgical forceps 110 having one or more electrodes for treating tissue of a patient. The electrosurgical forceps 110 includes a housing 111 and opposing jaw members 113 and 115 disposed at a distal end of a shaft 112. The jaw members 113 and 115 have one or more active electrodes 114 and a return electrode 116 disposed therein, respectively. The active electrode 114 and the return electrode 116 are connected to the generator 200 through cable 118 that includes the supply and return lines 14, 18 coupled to the active and return terminals 230, 232, respectively (FIG. 3). The electrosurgical forceps 110 is coupled to the generator 200 at a connector having connections to the active and return terminals 230 and 232 (e.g., pins) via a plug disposed at the end of the cable 118, wherein the plug includes contacts from the supply and return lines 14, 18 as described in more detail below.

Figure 2:
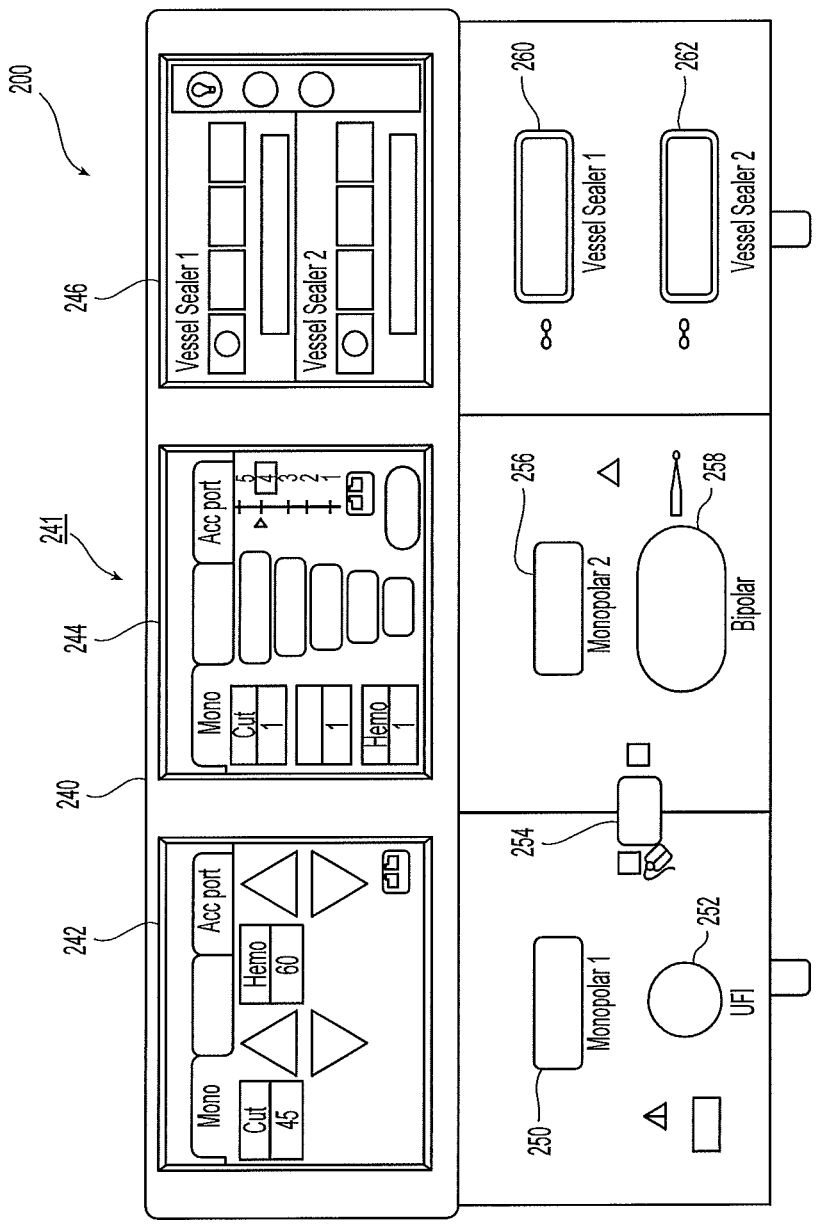
FIG. 2 is a front view of one embodiment of an electrosurgical generator according to the present disclosure.

With reference to FIG. 2, a front face 240 of the generator 200 is shown. The generator 200 may be any suitable type (e.g., electrosurgical, microwave, etc.) and may include a plurality of connectors 250-262 to accommodate various types of electrosurgical instruments (e.g., electrosurgical forceps 110, etc.).

The generator 200 includes a user interface 241 having one or more display screens or information panels 242, 244, 246 for providing the user with variety of output information (e.g., intensity settings, treatment complete indicators, etc.). Each of the screens 242, 244, 246 is associated with corresponding connector 250-262. The generator 200 includes suitable input controls (e.g., buttons, activators, switches, touch screen, etc.) for controlling the generator 200. The display screens 242, 244, 246 are also configured as touch screens that display a corresponding menu for the electrosurgical instruments (e.g., electrosurgical forceps 110, etc.). The user then adjusts inputs by simply touching corresponding menu options.

Screen 242 controls monopolar output and the devices connected to the connectors 250 and 252. Connector 250 is configured to couple to a monopolar electrosurgical instrument (e.g., electrosurgical instrument 12) and connector 252 is configured to couple to a foot switch (not shown). The foot switch provides for additional inputs (e.g., replicating inputs of the generator 200). Screen 244 controls monopolar and bipolar output and the devices connected to the connectors 256 and 258. Connector 256 is configured to couple to other monopolar instruments. Connector 258 is configured to couple to a bipolar instrument (not shown).

Screen 246 controls bipolar sealing procedures performed by the forceps 110 that may be plugged into the connectors 260 and 262. The generator 200 outputs energy through the connectors 260 and 262 suitable for sealing tissue grasped by the forceps 110. In particular, screen 246 outputs a user interface that allows the user to input a user-defined intensity setting. The user-defined setting may be any setting that allows the user to adjust one or more energy delivery parameters, such as power, current, voltage, energy, etc. or sealing parameters, such as energy rate limiters, sealing duration, etc. The user-defined setting is transmitted to the controller 224 where the setting may be saved in memory 226. In embodiments, the intensity setting may be a number scale, such as for example, from one to ten or one to five. In embodiments, the intensity setting may be associated with an output curve of the generator 200. The intensity settings may be specific for each forceps 110 being utilized, such that various instruments provide the user with a specific intensity scale corresponding to the forceps 110.

FIG. 3 shows a schematic block diagram of the generator 200 having a controller 224, a high voltage DC power supply 227 ("HVPS") and an RF output stage 228. The HVPS 227 is connected to an AC source (e.g., electrical wall outlet) and provides high voltage DC power to an RF output stage 228, which then converts high voltage DC power into RF energy and delivers the RF energy to the active terminal 230. The energy is returned thereto via the return terminal 232. In particular, the RF output stage 228 generates sinusoidal or rectangular waveforms of RF energy. The RF output stage 228 is configured to generate a plurality of waveforms having various duty cycles, peak voltages, waveform crest factors, and other suitable parameters. Certain types of waveforms are suitable for specific electrosurgical modes. For instance, the RF output stage 228 typically generates a 100% duty cycle sinusoidal waveform in cut mode, which is well-suited for ablating, fusing, and dissecting tissue and a 1-25% duty cycle waveform in coagulation mode, which is suitable for cauterizing tissue to stop bleeding.

The controller 224 includes a processor 225 operably connected to a memory 226, which may include transitory type memory (e.g., RAM) and/or non-transitory type memory (e.g., flash media, disk media, etc.). The processor 225 includes an output port that is operably connected to the power supply 227 and/or RF output stage 228 allowing the processor 225 to control the output of the generator 200 according to either open and/or closed control loop schemes. A closed loop control scheme is a feedback control loop, in which a plurality of sensors measure a variety of tissue and energy properties (e.g., tissue impedance, tissue temperature, output power, current and/or voltage, etc.), and provide feedback to the controller 224. The controller 224 then signals the power supply 227 and/or RF output stage 228, which adjusts the DC and/or power supply, respectively. Those skilled in the art will appreciate that the processor 225 may be substituted by using any logic processor (e.g., control circuit) adapted to perform the calculations and/or set of instructions described herein including, but not limited to, field programmable gate array, digital signal processor, and combinations thereof.

As used herein, the term "electrosurgical waveform" refers to a waveform output by the generator 200. The electrosurgical waveform may include a plurality of cycles outputted at the operating frequency of the generator 200, each of which includes a positive and a negative half cycle. The operating frequency of the generator 200 is the frequency at which the switching components of the inverter are toggled. The cycles may be grouped into "on" and "off" periods defined by a duty cycle of the electrosurgical waveform (e.g., 20% duty cycle denotes that cycles are output 20% of the time). The "on" periods may be output at a predetermined repetition rate, which is lower than the cycle rate (e.g., operating frequency) since the "on" periods include a plurality of cycles. As used herein, the term "crest factor" refers to a peak-to-average ratio of the waveform describing the shape of the waveform (e.g., a square waveform having positive and negative half cycles has a crest factor of 1 and a sinusoidal waveform having positive and negative half cycles has a crest factor of 1.414).

Figure 4:
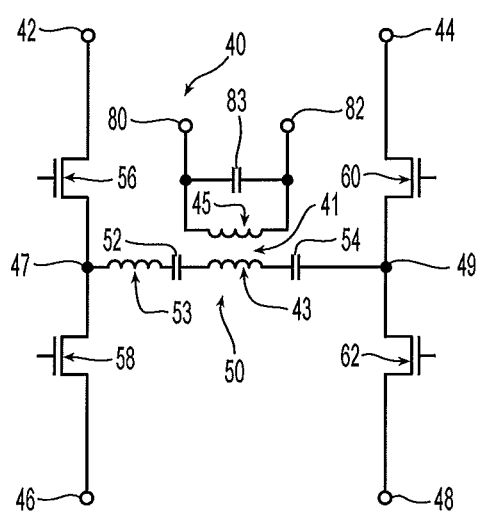
FIG. 4 is a schematic diagram of the circuitry for a modulated RF inverter of the electrosurgical generator of FIG. 2 according to the present disclosure.

In embodiments, the RF output stage 228 may be configured as a phase-shifted, pulse-width and/or frequency modulated RF inverter as shown in more detail in FIG. 4. In particular, the RF output stage 228 is shown as an H-bridge inverter including a bridge circuit 40. The bridge circuit 40 is coupled to the HVPS 227 and receives DC voltage therefrom. More specifically, the bridge circuit 40 includes an isolation transformer 41 having a primary winding 43 and a secondary winding 45. The primary winding 43 includes first and second connections 47 and 49. The first connection 47 includes a drain supply 42 and a source supply 46. The second connection 49 also includes a drain supply 44 and a source supply 48. The source supplies 46, 48 and drain supplies 42, 44 are coupled to the HVPS 227.

First connection 47 includes a first pair of switching components 56 and 58 and second connection 49 includes a second pair of switching components 60 and 62. The switching components 56, 58, 60, and 62 can be, for example, transistors, such as metal-oxide semiconductor field-effect transistors (MOSFET), insulated gate bipolar transistors (IGBT), relays, and the like.

The secondary winding 45 includes two output terminals 80 and 82. Output terminals 80, 82 may include a band pass filter 83 coupled therebetween. The first and second connections 47 and 49 are connected in series by a resonant network, e.g., a tank circuit 50. The tank circuit 50 may be a series resonant network that is arranged in an LCC configuration having an inductor 53 and capacitors 52 and 54 with the primary winding 43 being coupled between capacitors 52 and 54. In embodiments, the tank circuit 50 may be any other suitable resonant network, such as a parallel resonant network and may include a plurality of reactive and passive components.

Output terminals 80, 82 may be separately connected to active and return poles of monopolar, bipolar electrosurgical or ablation instruments (e.g., instrument 12, forceps 110). Additionally or alternatively, output terminals 80, 82 may share connections to a single active or return lead. In one embodiment, output terminal 82 is coupled to the return electrode 6, while output terminal 80 is coupled to active leads on either a single instrument or multiple instruments.

The switching components 56, 58, 60, 62 are coupled to the controller 224 (FIG. 3). The controller 224 drives the switching components 56, 58, 60, 62 at a predetermined frequency or frequencies to turn "on" and "off" at a range of predetermined frequencies which is also the operating frequency range of the generator 200, thereby closing and opening the first and second connections 47 and 49, respectively. The frequency at which the switching components 56, 58, 60, 62 are turned on and off is controlled by the controller 224. The controller 224 may include a pulse-width modulated driver for supplying a driver signal to each of the switching components 56, 58, 60, 62. The driver emits a phase-shifted drive signal having first and second components that are out of phase (e.g., 180° out-of-phase). Thus, each pair of the switching components (e.g., 56, 58 and 60, 62) has a phase relationship that is 180° out-of-phase with its opposing pair. In other words, the driver signal cycles each of the pairs of the switching components 56, 58 and 60, 62 between "on" and "off" positions at the same frequency but out of sync, to create two waveforms that are 180° out-of-phase at the first and second connections 47 and 49. In addition, the drive signals supplied to each pair of the switching components 56, 58 and 60, 62 are also phase-shifted with respect to each other to generate a plurality of waveforms of varying duty cycle. Therefore, adjusting the phase-shifted dual drive signals provides varying operating RF duty cycles or pulse-widths. Varying the duty cycle of the phase-shifted dual drive signals allows for better control of the RF amplitude and the average power delivered. Phase-shifting also allows for interleaving of power delivered to the output terminal pair 80 and 82. Further, when combined with the tank circuit 50, the pulse-width or frequency modulation may be used to vary the output voltage amplitude at the load.

The tank circuit 50 in combination with the primary winding 43 converts rectangular pulse-width modulated (e.g., AC energy having multiple high frequency components) energy into RF energy (e.g., AC energy having a single high frequency component from about 100 kHz to about 100,000 kHz). When the switching components 56, 58 and 60, 62 are closed, a high frequency pulse is supplied to the capacitors 52, 54 of the tank circuit 50. The tank circuit 50 converts the pulses into biphasic sinusoidal waveforms by the alternation of first and second connections 47 and 49. The tank circuit 50 can include a plurality of active components (e.g., inductors and capacitors) arranged in either parallel, series or combination thereof as described above.

During operation, primary winding 43 creates two half-sinusoidal waveforms of the same frequency, but with a variable phase with respect to each other, which then combine at a secondary winding 45 to form a full waveform. More specifically, each pair of the switching components 56, 58 and 60, 62 is driven by a drive signal supplied at a predetermined phase with respect to each other. Each pair of the switching components 56, 58 and 60, 62 is alternately switched "on" and "off" at the same frequency by the phase-shifted drive signals.

The processor 225 is coupled to the user interface 241 and is configured to modify modes, energy settings, and other parameters of the generator 200 in response to user input. The generator 200 is configured to operate in a variety of modes. In one embodiment, the generator 200 may output the following modes: cut, blend, coagulate, division with hemostasis, fulgurate, spray, combinations thereof, and the like. Each mode operates based on a pre-programmed power curve that controls the amount of power that is output by the generator 200 at varying impedances of the load (e.g., tissue). Each power curve includes power, voltage and current control ranges that are defined by the user-selected power setting and the measured impedance of the load.

In the cut mode, the generator 200 may supply a continuous sine wave output having a plurality of RF cycles at a predetermined frequency (e.g., 472 kHz) with a crest factor of about 1.414 over an impedance range of from about 100Ω to about 2,000Ω. The cut mode power curve may include three regions: constant current into low impedance, constant power into medium impedance and constant voltage into high impedance. In the blend mode, the generator may supply alternating bursts of a sine wave output at a predetermined periodic rate, with the burst cycles reoccurring at a first predetermined repetition rate (e.g., about 26.21 kHz), each burst cycle includes a plurality of sine wave RF cycles at the predetermined frequency (e.g., 472 kHz). In one embodiment, the duty cycle of the bursts may be about 50%. In other words, for each burst cycle the power is on for 50% of the time and it is off for 50% of the time. The crest factor of one period of the sine wave output may be about 1.414. The crest factor of one burst cycle may be about 2.7.

The division with hemostasis mode may include bursts of sine wave outputs at a predetermined frequency (e.g., 472 kHz) reoccurring at a second predetermined repetition rate (e.g., about 28.3 kHz). The duty cycle of the bursts may be about 25%, i.e. the power is on for 25% of each cycle and off for the remaining 75% of the cycle. The crest factor of one burst cycle may be about 4.3 across an impedance of from about 100Ω to about 2,000Ω. The fulgurate mode may include bursts of sine wave outputs at a predetermined frequency (e.g., 472 kHz) reoccurring at a third predetermined repetition rate (e.g., about 30.66 kHz). The duty cycle of the bursts may be about 6.5% and the crest factor of one burst cycle may be about 5.55 across an impedance range of from about 100Ω to about 2,000Ω. The spray mode may include bursts of a sine wave output at a predetermined frequency (e.g., 472 kHz) reoccurring at a fourth predetermined repetition rate (e.g., about 21.7 kHz). The duty cycle of the bursts may be about 4.6% and the crest factor of one burst cycle may be about 6.6 across the impedance range of from about 100Ω to about 2,000Ω.

The generator 200 provides closed-loop control of various electrosurgical modes, e.g., arc cutting and coagulation, based on current, power and voltage bounds inherent to voltage-current characteristics of a resonant inverter of the RF output stage 228. The voltage-current characteristic of any resonant inverter, when plotted, forms an ellipse bounded by voltage and current limited regions due to the output impedance of the resonant network. This output impedance of the inverter may be designed to be centered upon the geometric mean of the expected minimum to maximum terminating resistances observed during operation in the electrosurgical mode (e.g., the resistance of the tissue). The operating characteristics of the RF output stage 228 may then be aligned to coincide with the maximum voltage and current of the particular power setting requested by the user.

Conventional generators supply electrosurgical energy to tissue by pulsing the output voltage waveform at a fixed repetition rate to produce a desired crest factor for a given mode (e.g., coagulation mode) output by the generator. In this scenario, the repetition rate is fixed across all power, voltage, and current settings for the given output mode of the generator.

Pulsing the output voltage waveform at a fixed repetition rate presents a unique problem for closed-loop control of the output voltage waveform using a phase-shifted inverter. Specifically, above a certain duty cycle (e.g., 50% duty cycle), the output voltage waveform will reach a peak voltage and, once that peak voltage is reached, additional increases in phase-shift do not affect the peak voltage. Thus, for a given power setting, when the impedance of a load (e.g., tissue) decreases, the peak voltage remains constant while the crest factor of the output voltage waveform increases. This increase in crest factor may lead to stray arcing. During operation, arcing is generated to achieve desired surgical effects. High arc currents are well-suited for their hemostasis effects, however, to limit thermal transfer, it is also desirable to limit stray arcing to the target tissue by controlling the crest factor of the voltage output waveform. The present disclosure provides for phase-shifted inverters that are configured to control crest factor to achieve these goals. More specifically, the present disclosure provides for setting the repetition rate and phase-shift of a phase-shifted inverter to produce an output voltage waveform that reduces changes in the crest factor in response to changes in load impedance.

Figure 5A:
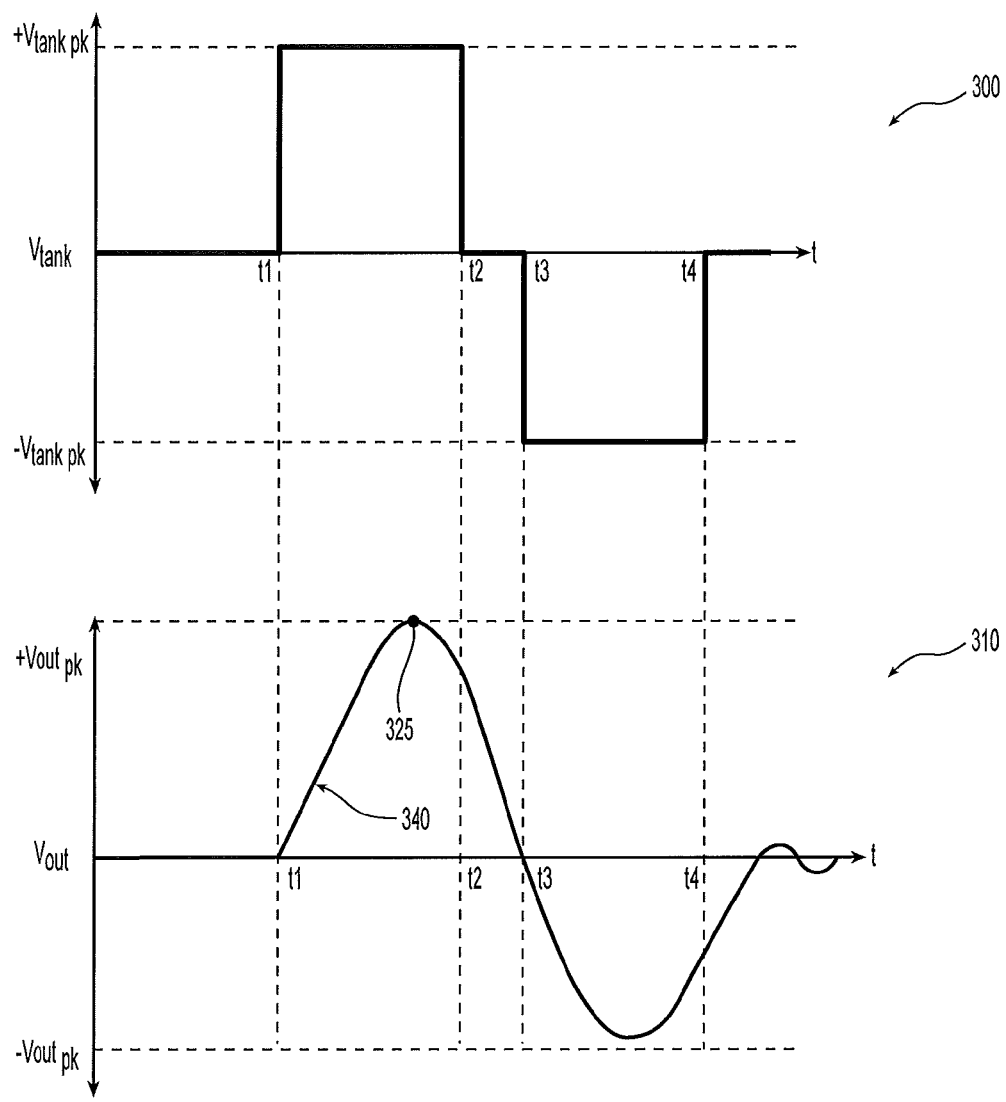
FIGS. 5A and 5B are overlapping plots of a tank voltage and an output voltage as a function of time according to an embodiment of a voltage source of the present disclosure.

Referring now to FIG. 5A, a plot 300 is shown illustrating a voltage of the tank circuit 50 (FIG. 4) or a so-called "tank voltage" ("Vtank") and a voltage output plot 310 showing a voltage output waveform ("Vout") from a voltage source, e.g., RF output stage 228, as a function time (t). At a time t1, one or both pairs of switching components 56, 58 and 60, 62 is turned "on" such that the tank voltage Vtank increases from zero volts to a positive peak voltage +Vtank$_{pk}$. At time t1, the voltage output Vout is at zero volts and increases until reaching a positive peak voltage +Vout$_{pk}$, depicted by a point 325 on plot 310. At a time t2, the output voltage Vout is decreasing while one or both pairs of switching components 56, 58 and 60, 62 is turned "off" such that the tank voltage Vtank decreases from +Vtank$_{pk}$ to zero volts. That is, while Vtank is at peak voltage Vtank$_{pk}$, the output voltage Vout increases to its peak voltage Vout$_{pk}$ and starts to decrease prior to Vtank decreasing to zero volts at time t2. At a time t3, one or both pairs of switching components 56, 58 and 60, 62 is turned "on" such that the tank voltage Vtank increases from zero volts to a negative peak voltage −Vtank$_{pk}$. At time t3, the voltage output Vout is at zero volts and decreasing toward achieving a negative peak voltage −Vout$_{pk}$. The response of the negative Vout is substantially similar to the above-described response of the positive half cycle of Vout.

The magnitude of the peak output voltage Vout$_{pk}$ is determined at least in part by the frequency response of the tank circuit 50 (FIG. 4) in the bridge circuit 40 and the load (e.g., tissue). Thus, the output voltage Vout will follow the step response of the tank circuit 50 due to the pulse of the tank voltage Vtank. The duration of the tank voltage Vtank pulse determines how long the output voltage Vout rises during each half cycle as shown by a portion 340 of the Vout plot 310 and, thus, to what extent the peak output voltage Vout$_{pk}$ increases. For relatively long duty cycles (e.g., 50% or greater duty cycle), the output voltage Vout rings up to a maximum-achievable peak 325 and starts to ring back down before the end of the Vtank pulse. If the duty-cycle is relatively short (e.g., less than 50% duty cycle), then the pulse does not last long enough for the output voltage Vout to reach its maximum-achievable peak. This allows the peak output voltage Vout$_{pk}$ to be controlled over a given range of duty cycles by controlling the duty cycle of the output voltage waveform Vout.

In some embodiments, the crest factor of the voltage output waveform Vout may be controlled by setting the repetition rate for a given power, voltage, and/or current setting of a generator and/or a given phase-shift setting of the bridge circuit 40. By setting the repetition rate, the duty cycle of the bridge circuit 40 may be controlled such that the output voltage Vout is increasing when the tank voltage Vtank is equal to zero volts upon turning "off" one or both pairs of switching components 56, 58 and 60, 62 of the bridge circuit 40. For example, the repetition rate may be increased or decreased for a particular output setting (e.g., power, voltage, current, etc.) of a generator 200 to decrease or increase, respectively, the duty cycle of the electrosurgical waveform.

Figure 5B:
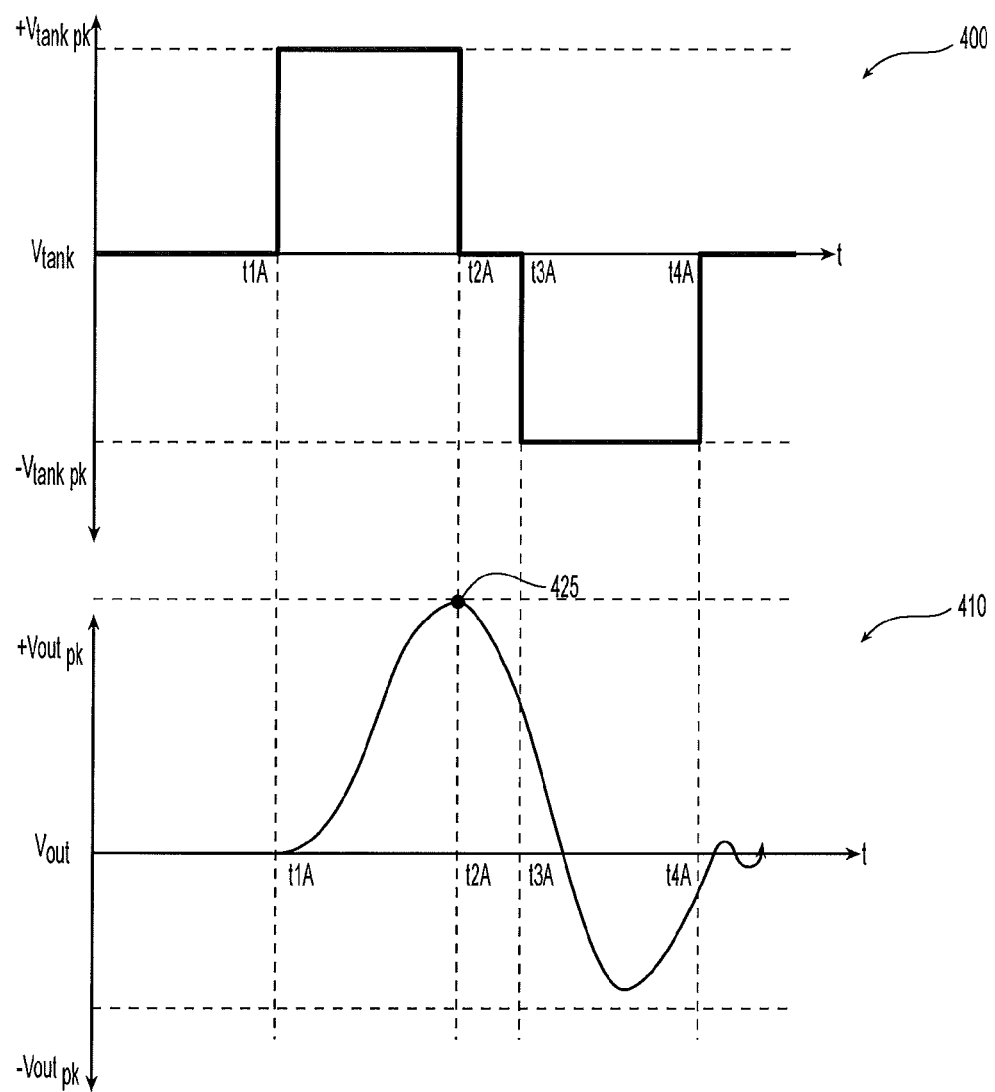

FIG. 5B shows a plot 400 of the tank voltage Vtank of the tank circuit 50 and a plot 410 of a voltage output waveform Vout from a voltage source, e.g., RF output stage 228, as a function time (t). At a time t1A, one or both pairs of switching components 56, 58 and 60, 62 is turned "on" such that the tank voltage Vtank increases from zero volts to a positive peak voltage +Vtank$_{pk}$. At time t1A, the voltage output Vout is at zero volts and increases until a positive peak voltage +Vout$_{pk}$, depicted by a point 425 on plot 410. At a time t2A, the voltage output Vout is increasing while one or both pairs of switching components 56, 58 and 60, 62 is turned "off" such that the tank voltage Vtank decreases from +Vtank$_{pk}$ to zero volts. At time t2A, the output voltage Vout reaches its positive peak +Vout$_{pk}$, depicted by a point 425 on plot 410. At time t3A, one or both pairs of switching components 56, 58 and 60, 62 is turned "on" such that the tank voltage Vtank decreases from zero volts to reach its negative peak −Vtank$_{pk}$. In contrast to plot 410 depicted in FIG. 5B, the duty cycle of the voltage output waveform Vout depicted by plot 310 of FIG. 5A is set such that output voltage waveform Vout is decreasing when Vtank decreases from Vtank$_{pk}$ to zero volts at time t2. FIG. 5B illustrates the effect of decreasing the duty cycle, relative to the duty cycle of FIG. 5A. In particular, increasing the repetition rate decreases the duty cycle of the voltage output waveform Vout to maintain the same RMS voltage. By decreasing the duration of the tank voltage Vtank pulse, the output voltage Vout is effectively prevented from reaching its maximum-achievable peak. Therefore, in this scenario, the peak output voltage Vpeak is controlled by the duty cycle. The response of the negative Vout is substantially similar to the above-described response of the positive half cycle of Vout.

While several embodiments of the disclosure have been shown in the drawings and/or described herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method for controlling an electrosurgical generator, the method comprising:
    generating at least one electrosurgical waveform at a selected energy setting through an RF output stage comprising an RF inverter coupled to a power source, the at least one electrosurgical waveform having a duty cycle and a crest factor;
    adjusting a repetition rate of the at least one electrosurgical waveform based on the selected energy setting to regulate the duty cycle of the at least one electrosurgical waveform;
    applying the at least one electrosurgical waveform to tissue through at least one electrode;
    measuring an output voltage of the at least one electrosurgical waveform; and supplying a control signal to the RF inverter based on the repetition rate when the output voltage is increasing to regulate the crest factor of the at least one electrosurgical waveform.

2. The method according to claim 1, further comprising:
calculating a peak value of the output voltage; and
supplying the control signal to the RF inverter prior to the output voltage reaching the peak value.

3. The method according to claim 2, wherein the peak value of the output voltage is changed based on the supplying of the control signal to the RF inverter.

4. The method according to claim 1, wherein the energy setting is at least one of power, current, and voltage.

5. The method according to claim 1, wherein the RF inverter comprises at least one switching element coupled to a controller.

6. The method according to claim 5, wherein the control signal is a phase-shifted drive signal generated by a pulse-width modulated driver for controlling the at least one switching element.

7. The method according to claim 1, further comprising increasing the repetition rate of the at least one electrosurgical waveform to decrease the duty cycle of the at least one electrosurgical waveform.

8. An electrosurgical generator, comprising:
an RF output stage comprising an RF inverter coupled to a power source, the RF output stage configured to generate at least one electrosurgical waveform at a selected energy setting, the at least one electrosurgical waveform having a duty cycle and a crest factor;
a controller configured to adjust a repetition rate of the at least one electrosurgical waveform based on the selected energy setting to regulate the duty cycle of the at least one electrosurgical waveform; and
a sensor configured to measure an output voltage of the at least one electrosurgical waveform, the controller configured to supply a control signal to the RF inverter based on the repetition rate when the output voltage is increasing to regulate the crest factor of the at least one electrosurgical waveform.

9. The electrosurgical generator according to claim 8, wherein the controller is further configured to calculate a peak value of the output voltage and supply the control signal to the RF inverter prior to the output voltage reaching the peak value.

10. The electrosurgical generator according to claim 9, wherein the peak value of the output voltage is changed based on the supplying of the control signal to the RF inverter.

11. The electrosurgical generator according to claim 8, wherein the energy setting is at least one of power, current, and voltage.

12. The electrosurgical generator according to claim 8, wherein the RF inverter comprises at least one switching element coupled to the controller.

13. The electrosurgical generator according to claim 12, wherein the control signal is a phase-shifted drive signal generated by a pulse-width modulated driver for controlling the at least one switching element.

14. The electrosurgical generator according to claim 8, wherein the controller is configured to increase the repetition rate of the at least one electrosurgical waveform to decrease the duty cycle of the at least one electrosurgical waveform.

15. An electro surgical system, comprising:
an electrosurgical generator comprising:
an RF output stage comprising an RF inverter coupled to a power source, the RF output stage configured to generate at least one electrosurgical waveform at a selected energy setting, the at least one electrosurgical waveform having a duty cycle and a crest factor;
a controller configured to adjust a repetition rate of the at least one electrosurgical waveform based on the selected energy setting to regulate the duty cycle of the at least one electrosurgical waveform; and
a sensor configured to measure an output voltage of the at least one electrosurgical waveform, the controller configured to supply a control signal to the RF inverter based on the repetition rate when the output voltage is increasing to regulate the crest factor of the at least one electrosurgical waveform.

16. The electrosurgical system according to claim 15, wherein the controller is further configured to calculate a peak value of the output voltage and supply the control signal to the RF inverter prior to the output voltage reaching the peak value.

17. The electrosurgical generator according to claim 16, wherein the peak value of the output voltage is changed based on the supplying of the control signal to the RF inverter.

18. The electrosurgical generator according to claim 15, wherein the energy setting is at least one of power, current, and voltage.

19. The electrosurgical system according to claim 15, wherein the RF inverter comprises at least one switching element coupled to the controller.

20. The electrosurgical system according to claim 19, wherein the control signal is a phase-shifted drive signal generated by a pulse-width modulated driver for controlling the at least one switching element.

* * * * *